(12) United States Patent
Harari et al.

(10) Patent No.: US 6,602,260 B2
(45) Date of Patent: Aug. 5, 2003

(54) POWERED BONE SCREW DEVICE

(75) Inventors: Boaz Harari, Haifa (IL); Kimberly A. Anderson, Eagan, MN (US); Karny Jacoby, Seattle, WA (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 09/776,545

(22) Filed: Feb. 2, 2001

(65) Prior Publication Data

US 2002/0107525 A1 Aug. 8, 2002

(51) Int. Cl.[7] ............................................... A61B 17/88
(52) U.S. Cl. ...................................... 606/104; 606/232
(58) Field of Search ................... 606/104, 232, 606/233; 81/436, 54, 57, 57.11, 57.14

(56) References Cited

U.S. PATENT DOCUMENTS

| | | | |
|---|---|---|---|
| 3,973,605 A | * 8/1976 | DeCaro | ..................... 81/429 |
| 4,632,100 A | 12/1986 | Somers et al. | |
| 4,941,466 A | 7/1990 | Romano | |
| 5,002,546 A | 3/1991 | Romano | |
| 5,142,954 A | * 9/1992 | Starke | ..................... 81/429 |
| 5,354,298 A | 10/1994 | Lee et al. | |
| 5,364,408 A | 11/1994 | Gordon | |
| 5,464,407 A | 11/1995 | McGuire | |
| 5,520,700 A | 5/1996 | Beyar et al. | |
| 5,584,860 A | * 12/1996 | Goble et al. | ................ 606/232 |
| 5,611,515 A | 3/1997 | Benderev et al. | |
| 5,643,320 A | * 7/1997 | Lower et al. | ............... 606/232 |
| 5,674,247 A | 10/1997 | Sohn | |
| 5,782,862 A | * 7/1998 | Bonutti | ..................... 606/232 |
| 5,814,051 A | * 9/1998 | Wenstrom, Jr. | ............. 606/104 |
| 5,836,314 A | 11/1998 | Benderev et al. | |
| 5,842,478 A | 12/1998 | Benderev et al. | |
| 5,860,425 A | 1/1999 | Benderev et al. | |

(List continued on next page.)

FOREIGN PATENT DOCUMENTS

GB 2 268 690 A 7/1993

OTHER PUBLICATIONS

Cespedes et al., Male Slings for Postprostatectomy Incontinence, Techniques in Urology vol. 7, No. 2, pp. 176–183 (2001).

Franco et al., Suburethral Sling for Male Urinary Incontinence, Infections in Urology vol. 14 No. 1, 7 pages (May/Jun. 2001).

InVance™ Male Sling System, Training Manual, American Medical Systems, 70 pages (Mar. 12, 2001).

Jacoby et al., Male Sling: A Multicenter Retrospective Analysis, Western Section AUA, pp. 86 (Sep. 2001).

Jacoby et al., Male Sling: A New Perineal Approach, 1 page (no date).

Kovac et al., Pubic Bone Suburethral Stabilization Sling: A Long–Term Cure for SUI?, Contemporary OB/GYN, pp. 1–8 (Feb. 1998).

Madjar et al., Bone Anchored Sling for the Treatment of Post/Prostatectomy Incontinence, Abstract, 1 page (Aug. 23, 1999).

(List continued on next page.)

*Primary Examiner*—Kevin Shaver
*Assistant Examiner*—Michael B. Priddy
(74) *Attorney, Agent, or Firm*—Jeffrey J. Hohenshell

(57) ABSTRACT

A medical screwdriver for inserting a medical screw connected to a suture into a bone. The screwdriver includes a shaft adapted to hold a medical screw at its distal end, a motor adapted to rotate the shaft, and a suture-receiving channel leading from the distal end of the shaft to a point distanced from the distal end of the shaft by at least 50% of the length of the shaft.

13 Claims, 6 Drawing Sheets

U.S. PATENT DOCUMENTS

| | | | |
|---|---|---|---|
| 5,972,000 A * | 10/1999 | Beyar et al. ................ | 606/139 |
| 6,241,736 B1 | 6/2001 | Sater et al. | |
| 6,264,676 B1 | 7/2001 | Gellman et al. | |
| 6,282,998 B1 * | 9/2001 | Beach ........................ | 81/437 |
| 6,322,492 B1 | 11/2001 | Kovac | |
| 6,328,686 B1 | 12/2001 | Kovac | |
| 6,328,744 B1 | 12/2001 | Harari et al. | |
| 6,334,446 B1 | 1/2002 | Beyar | |
| 6,382,214 B1 | 5/2002 | Raz et al. | |
| 6,387,041 B1 | 5/2002 | Harari et al. | |
| 6,406,480 B1 | 6/2002 | Beyar et al. | |
| 6,423,072 B1 * | 7/2002 | Zappala ..................... | 606/104 |
| 2001/0010008 A1 | 7/2001 | Gellman et al. | |
| 2001/0012941 A1 | 8/2001 | Beyar et al. | |
| 2001/0027321 A1 | 10/2001 | Gellman et al. | |
| 2001/0029376 A1 | 10/2001 | Sater et al. | |
| 2001/0041895 A1 | 11/2001 | Beyar et al. | |
| 2002/0035369 A1 | 3/2002 | Beyar et al. | |
| 2002/0050277 A1 | 5/2002 | Beyar | |
| 2002/0095064 A1 | 7/2002 | Beyar | |
| 2002/0095163 A1 | 7/2002 | Beyar | |
| 2002/0095181 A1 | 7/2002 | Beyar | |

OTHER PUBLICATIONS

Madjar et al., Bone Anchored Sling for the Treatment of Post–Prostatectomy Incontinence, The Journal of Urology, vol. 165, No. 1, pp. 72–76 (Jan. 2001).

Precision Tack, Transvaginal Anchor System, The Precise Approach to Transvaginal Sling Procedure (advertisement), Boston Scientific Corporation, Microvasive, 4 pages (Jun. 1998).

Precision Twist, Transvaginal Anchor System, Low Profile Design for Precise Anchor Placement (advertisement), Boston Scientific Corporation, Microvasive, 4 pages (Jun. 1998).

Vesica Sling Kits, Simplifying Sling Procedures, Boston Scientific Microvasive, 4 pages (1998).

Vesica Sling Kits, A New Approach to Bladder Neck Suspension, Boston Scientific Microvasive, 4 pages (1995).

* cited by examiner

POWERED BONE SCREW DEVICE

BACKGROUND OF THE INVENTION

Attaching a suture to a bone is a task that is well known in the art of surgery. A common solution is to screw a threaded screw, to which the suture is attached, into the bone. However, screwdrivers used to perform this task may injure tissue surrounding the bone. In addition, during the insertion of the screw the suture dangles from the screw and may get stuck or otherwise interfere with the surgeon's operations.

BRIEF SUMMARY OF THE INVENTION

An aspect of some embodiments of the invention relates to a medical screwdriver which includes a long bore, in which a suture may reside while an anchor screw holding the suture is screwed into a bone. The bore is optionally at least a few centimeters long such that movements of the suture are sufficiently distanced from the bone and its surrounding flesh.

In some embodiments of the invention, the bore runs along the rotation axis of the screwdriver. Having the bore run along the rotation axis of the screwdriver minimizes the rotation of the suture, such that the suture does not substantially move and therefore does not hit flesh of the patient. In addition, when the suture does not substantially rotate there is substantially no danger of tearing and/or knotting due to rotation. In some embodiments of the invention, the bore is defined by a hollow shaft that turns the screw. Alternatively, the bore is defined by a hollow shaft, which runs parallel to the rotation axis of the screwdriver. For example, the hollow shaft carrying the suture may be connected to a sheath, which isolates a shaft of the screwdriver from a patient's flesh. In some embodiments of the invention, the bore has a ring shape which is defined between a shaft which turns the screw and a sheath which isolates the shaft which turns the screw from the flesh surrounding the bone.

An aspect of some embodiments of the invention relates to a stationary sheath for isolating a shaft of a medical screwdriver from surrounding tissue. The stationary sheath prevents the rotating shaft of the screwdriver from injuring tissue surrounding a bone into which a screw is inserted. Optionally, the sheath is rotationally locked to the screwdriver body.

Optionally, the stationary sheath comprises a collapsible shield cap, which surrounds a screw held by the screwdriver when the screw is not pressed against a bone.

There is therefore provided in accordance with an embodiment of the present invention, a medical screwdriver for inserting a medical screw connected to a suture into a bone, including a shaft adapted to hold a medical screw at its distal end, a motor adapted to rotate the shaft, and a suture-receiving channel leading from the distal end of the shaft to a point distanced from the distal end of the shaft by at least 50% of the length of the shaft.

Optionally, the suture-receiving channel leads to a point distanced from the distal end of the shaft by the length of the shaft. In some embodiments of the invention, the suture-receiving channel comprises a through bore defined in the shaft. Optionally, the hollow shaft is coupled to the motor through a gear pair and/or through a shaft housing which defines a bore therethrough. In some embodiments of the invention, the motor is held in a casing which defines a through channel, which channel leads from a first side of the casing close to a coupling to the hollow shaft to an opposite side of the casing.

Optionally, the screwdriver includes a switch having a first position in which a suture located in the channel is held tightly and a second position in which the suture is free to move.

Optionally, the screwdriver includes a stationary sheath that surrounds the shaft. Optionally, the stationary sheath is removable. In some embodiments of the invention, the stationary sheath comprises a key, which is adapted to fit in a respective notch in a casing of the motor. Optionally, the channel is defined between the stationary sheath and the shaft. Optionally, the stationary sheath comprises a distal collapsible shield, which is adapted to cover, in the absence of an axially applied force, at least a portion of a screw held by the shaft.

There is further provided in accordance with an embodiment of the present invention, a medical screwdriver for inserting a medical screw connected to a suture into a bone, comprising a shaft adapted to hold a medical screw at its distal end, a stationary sheath which surrounds the shaft and a motor adapted to rotate the shaft so as to push the screw into a bone. Optionally, the stationary sheath comprises a distal collapsible shield, which is adapted, in the absence of force, to cover at least a portion of a screw held by the shaft.

There is further provided in accordance with an embodiment of the present invention, a stationary sheath, comprising a sheath, a collapsible shield connected at a distal end of the sheath and a rotation stopper that prevents the sheath from rotating. Optionally, the rotation stopper comprises a key protruding from a proximal end of the sheath, which key is adapted to fit into a compatible grove of a screwdriver. In some embodiments of the invention, the sheath defines a slot and the rotation stopper comprises a rod, which is adapted to fit into the slot and to connect to a screwdriver. Optionally, the sheath is at least two centimeters long.

BRIEF DESCRIPTION OF THE DRAWINGS

Exemplary non-limiting embodiments of the invention will now be described with reference to the following description in conjunction with the figures, wherein identical structures, elements or parts which appear in more than one figure are optionally labeled with a same or similar numeral in all the figures in which they appear, in which.

DETAILED DESCRIPTION OF THE INVENTION

Figure 1:
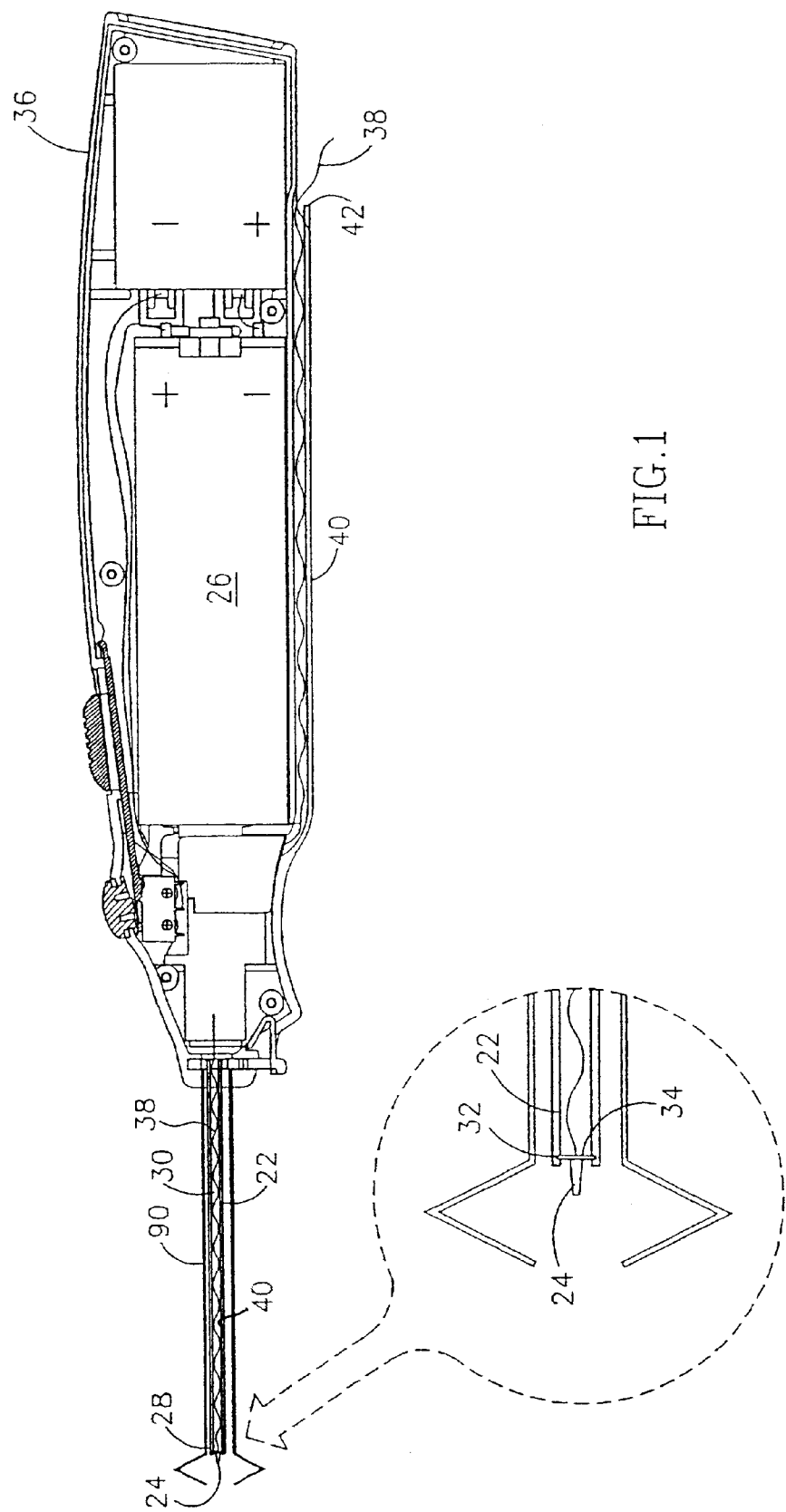
FIG. 1 is a schematic illustration of a medical screwdriver, in accordance with an exemplary embodiment of the invention.

FIG. 1 is a schematic illustration of a medical screwdriver 20, in accordance with an exemplary embodiment of the invention. Screwdriver 20 comprises a shaft 22 that grasps a screw 24, which is to be inserted into a bone. Optionally, a distal tip 28 of shaft 22 comprises an elastic material that tightly grasps screw 24. Alternatively or additionally, distal tip 28 comprises a magnet which grasps screw 24. In some embodiments of the invention, distal tip 28 comprises a circumferential groove 32 that receives a head 34 of screw 24. Alternatively or additionally, distal tip 28 comprises a perpendicular bar which fits into a groove in head 34 of screw 24. A motor 26 is coupled to shaft 22 such that when the motor is actuated shaft 22 rotates screw 24.

In some embodiments of the invention, shaft 24 defines an internal, central, through bore 30. Bore 30 is adapted to receive a suture 38 which is attached to screw 24. A body 36 of screwdriver 20 optionally also includes a channel 40 in which suture 38 resides during the operation of screwdriver 20. Thus, suture 38 does not dangle in the proximity of the bone into which screw 24 is being inserted and/or near open flesh surrounding the bone, while screw 24 is revolving. Thus, suture 38 cannot cause damage to flesh of the patient to which the screw is inserted and/or entangle on any other object.

In some embodiments of the invention, suture 38 is attached to screw 24 before the screw is placed within distal tip 28 of shaft 22. Optionally, in placing screw 24 in screwdriver 24, a leading elastic stick (not shown) is attached to a distal end (i.e., far from screw 24) of suture 38, and the elastic stick is used to push suture 38 through bore 30 and channel 40 to a distal end 42 of channel 40. Alternatively or additionally, the leading elastic stick is passed from distal end 42 of channel 40 to tip 28 where it is attached to suture 38. The leading elastic stick is then pulled out of channel 40 with suture 38. Further alternatively or additionally, suture 38 is inserted to bore 30 and/or channel 40 before it is attached to screw 24.

After screw 24 is inserted into the bone, tip 28 releases head 34 of screw 24 and screwdriver 20 is optionally pulled away from screw 24, allowing suture 38 to come out of bore 30.

In some embodiments of the invention, a stationary sheath 90 surrounds shaft 22, such that while shaft 22 rotates it does not injure surrounding flesh. Stationary sheath 90 is optionally anchored to body 36 as described hereinbelow with reference to FIG. 3.

Figure 2A:
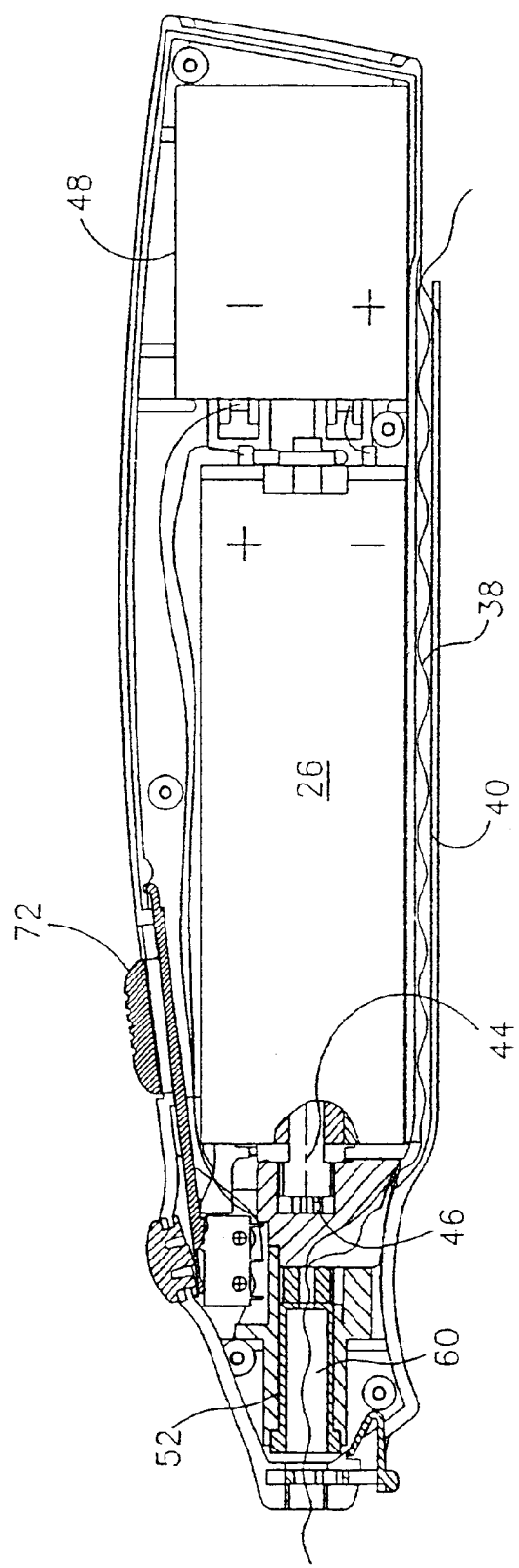
FIGS. 2A and 2B are schematic illustrations of a body of the screwdriver of FIG. 1, in accordance with an embodiment of the present invention.
Figure 2B:
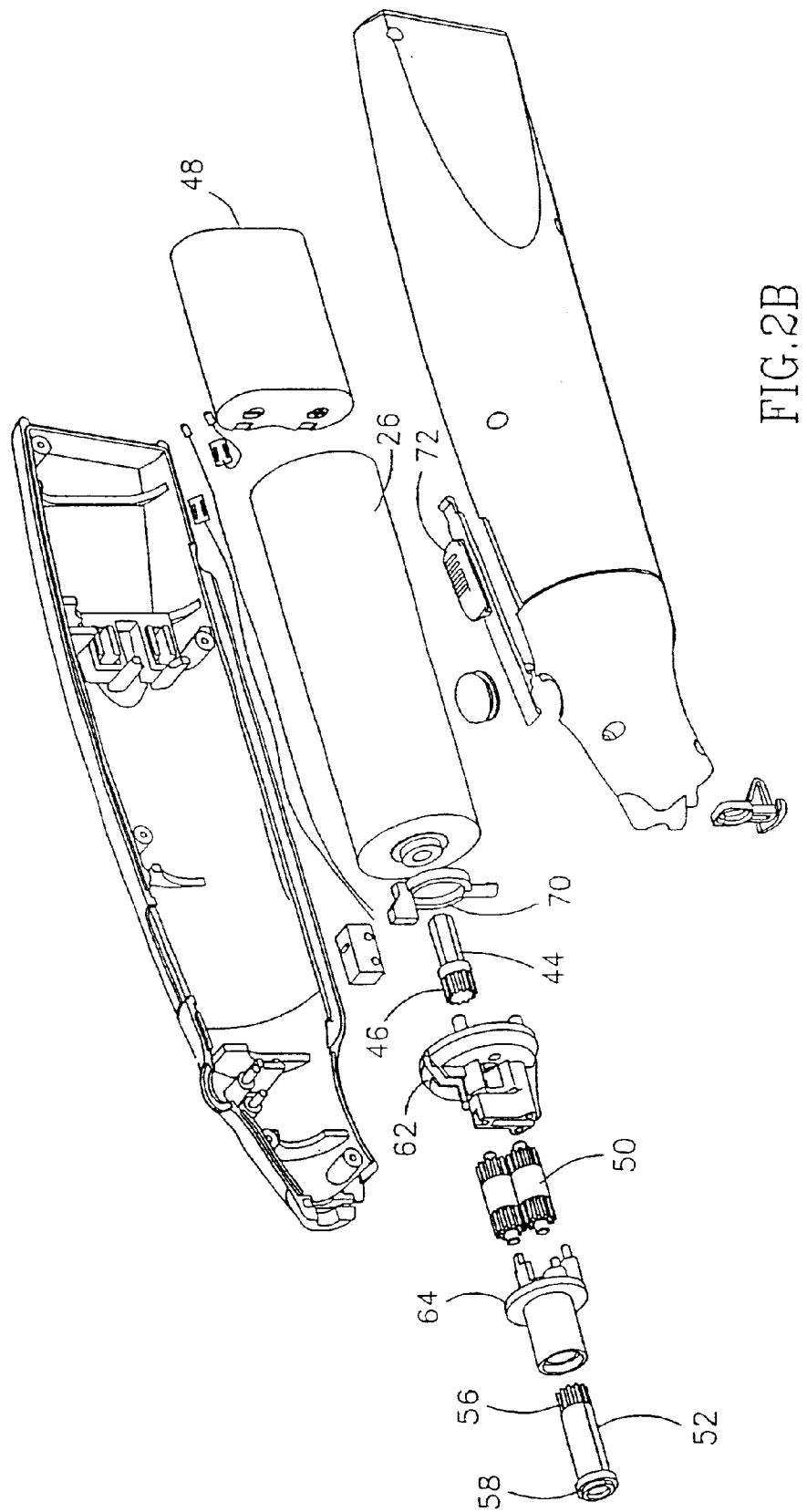

FIG. 2A is a schematic cross section view of body 36 of screwdriver 20, in accordance with an embodiment of the present invention. Reference is also made to FIG. 2B which is a schematic exploded perspective view of the pieces of body 36, in accordance with an embodiment of the present invention. Motor 26 is optionally powered by a battery 48 (FIG. 2B), for example a lithium rechargeable battery, although substantially any other battery may be used. Alternatively or additionally, a plurality of batteries and/or a cord power supply are used.

In some embodiments of the invention, the transfer of rotational movements from motor 26 to shaft 22 includes a by-passing set-up which allows suture 38 to lay along a path between bore 30 and channel 40 while motor 26 operates. Optionally, the by-passing set-up comprises a pair of gears 50 which are situated on opposite sides of the longitudinal axis of shaft 22. In some embodiments of the invention, the gears 50 are located on horizontal sides of the longitudinal axis of shaft 22, allowing the suture to fall into channel 40 without guidance. Alternatively, the gears 50 are located on vertical sides or at any other location relative to the longitudinal axis. The use of a pair of gears provides a relatively stable transfer of force from motor 26 to shaft 22.

Figure 2C:
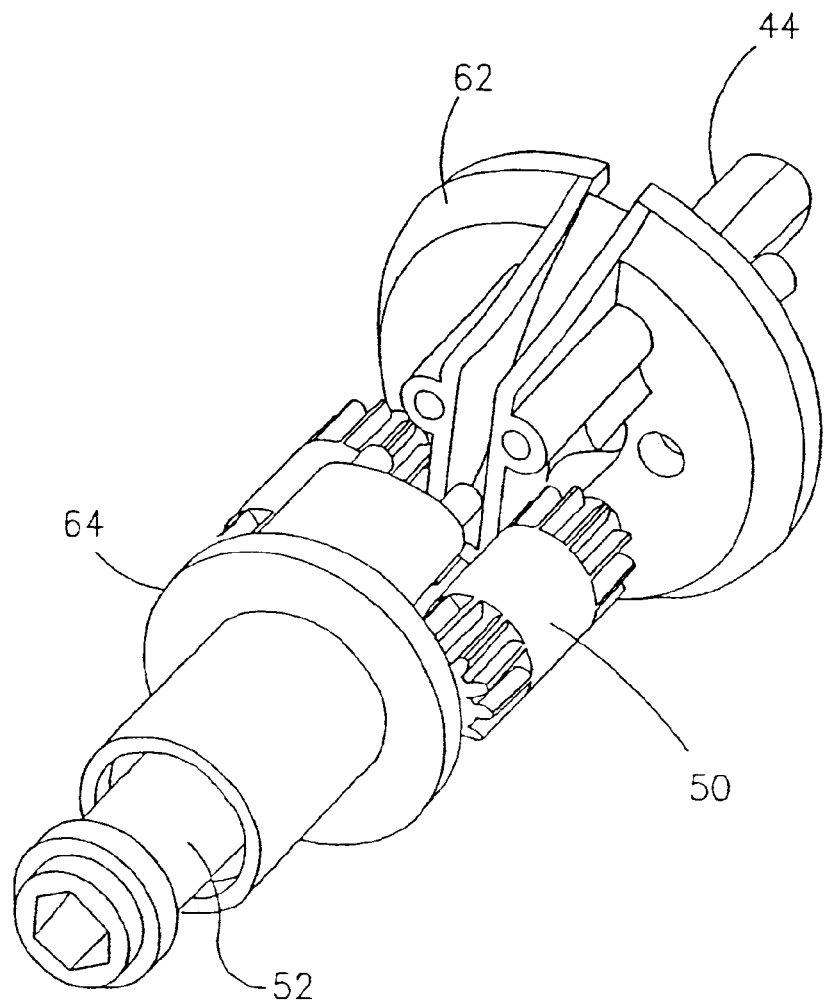
FIG. 2C is a schematic illustration of a set of gears for transferring power in a medical screwdriver, in accordance with an embodiment of the present invention.

Reference is also made to FIG. 2C which is a schematic illustration of the connections of gears 50, in accordance with an embodiment of the present invention. In an exemplary embodiment of the present invention, motor 26 rotates a motor shaft 44 which comprises a gear head 46 that interlocks into the pair of gears 50. Shaft 22 fits into a shaft housing 52 having a proximal gear 56 which interlocks into the other end of the pair of gears 50. Optionally, shaft housing 52 comprises a hexagonal receptacle 58 which tightly receives shaft 22 (FIG. 1). Alternatively, shaft 52 comprises any other shaped receptacle and/or other attachment device for receiving shaft 22. Similarly to shaft 22, shaft housing 52 comprises a bore 60 which has a common axis with bore 30 of shaft 22 (FIG. 1).

Alternatively to using gear pair 50, motor shaft 44 is held (e.g., by body 36 and/or motor 26) above, under or to the side of the longitudinal axis of shaft 22, such that gear head 46 of motor shaft 44 interlocks into proximal gear 56 of shaft housing 52. Thus, motor shaft 44 and shaft housing 52 or in a step configuration which allows suture 38 to pass out of shaft housing 52 into channel 40.

In some embodiments of the invention, a casing of body 36 defines channel 40 along a side of the body. Alternatively, channel 40 is defined within the casing of body 36 or is defined by an external piece attached to body 36.

In some embodiments of the invention, the pair of gears 50 is situated on a side of proximal gear 56 and gear head 46 such that they allow free passage of suture 38 between bore 60 and channel 40. Optionally, a distributor 62 leads suture 38 between bore 60 and channel 40 without entangling in gears 46 and 50. In some embodiments of the invention, a protective piece 64 prevents suture 38 from entangling within any of gears 56 and 50.

In some embodiments of the invention, a stopper 70 which is connected to a user switch 72 can firmly grasp suture 38 so as to prevent the suture from moving, for example while inserting the screw to the bone.

Alternatively to inserting screw 24 to the bone with suture 38 already tied to the screw, suture 38 is tied to the screw after the screw is inserted to the bone, using bore 30 and channel 40. Optionally, a suture leader (not shown) is used to push suture 38 through channel 40 and bore 30 to screw 24. In some embodiments of the invention, screw 24 comprises resilient arms which receive the suture when it is pushed through bore 30. Alternatively, screw 24 comprises any other device for attaching to a suture which tightly connects to sutures approaching the head of the screw in the direction of the long axis of the screw. Optionally, suture 38 is inserted with a loop tied at its end. Alternatively, suture 38 is inserted doubled over in a manner which pushes ahead a U shape. Further alternatively, a miniature ring, such as a key chain ring, is tied to the distal end of the suture when it is pushed through bore 30. Alternatively or additionally, screw 24 comprises a loop into which suture 38 is threaded by the suture leader.

Figure 3:
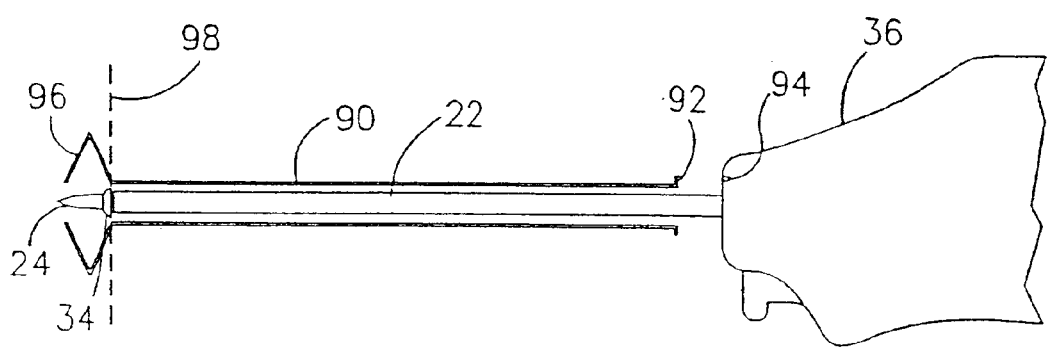
FIG. 3 is a schematic illustration of a sheath surrounding a shaft of a screwdriver, in accordance with some embodiments of the present invention.

FIG. 3 is a schematic illustration of sheath 90, in accordance with an embodiment of the present invention. Sheath 90 optionally comprises a key 92 which fits into a respective notch 94 in body 36 of screwdriver 20. Optionally, sheath 90 is a disposable detachable sheath which is easily replaced. Alternatively or additionally, sheath 90 is firmly and/or permanently anchored to screwdriver body 36 to prevent falling during use. In some embodiments of the invention, before each screw insertion, a separate sterile sheath 90 is placed around shaft 22.

In some embodiments of the invention, sheath 90 comprises, at a distal end thereof, a collapsible shield 96 which has an open state in which it entirely covers screw 24 and a closed state in which it collapses onto a line 98 about at the location of head 34 of the screw. When screw 24 is pressed against a bone, the distal edges of collapsible shield 96 are pushed back while screw 24 enters the bone. When, however, screwdriver 20 is pulled away from the bone, collapsible shield 96 expands to cover screw 24 and prevent inadvertent damage to patient tissue. Optionally, the collapsible shield comprises a tube in which a plurality, e.g., between four and sixteen, of axial slots are cut.

In some embodiments of the invention, sheath 90 comprises a durable plastic, such as polyurethane, polypropylene and/or any other rigid biocompatible plastic. Alternatively or additionally, sheath 90 comprises any other suitable material. Optionally, collapsible shield 96 comprises the same material as sheath 90 and possibly is produced as an integral part of sheath 90.

The inner wall of sheath 90 is optionally distanced from shaft 22 by a small distance which prevents sheath 90 from touching rotating shaft 22. Optionally, the distance between the inner wall of sheath 90 and shaft 22 is smaller than a predetermined distance, e.g., 1 mm, so that the total diameter of shaft 22 with sheath 90 is not substantially increased by using sheath 90. In addition, sheath 90 is also relatively thin. In some embodiments of the invention, sheath 90 covers the entire length of shaft 22. Optionally, shaft 22 and sheath 90 are over 2, 4 or even 6 centimeters long so that screwdriver body 36 is not brought too close to the patient's bone.

In some embodiments of the invention, shaft 22 does not define a bore 30, but rather suture 38 is confined between shaft 22 and sheath 90. Alternatively or additionally, shaft 22 defines a partial bore within a distal portion thereof. Suture 38 passes through the distal portion and emerges therefrom to be confined between sheath 90 and shaft 22. Optionally, sheath 90 comprises, at its distal end, a hole or slot through which suture 38 exits the area between sheath 90 and shaft 22. The distal bore of shaft 22 optionally runs over a short distance (e.g., 0.5 cm), half the length of shaft 22 or most of the length of shaft 22.

Figure 4:
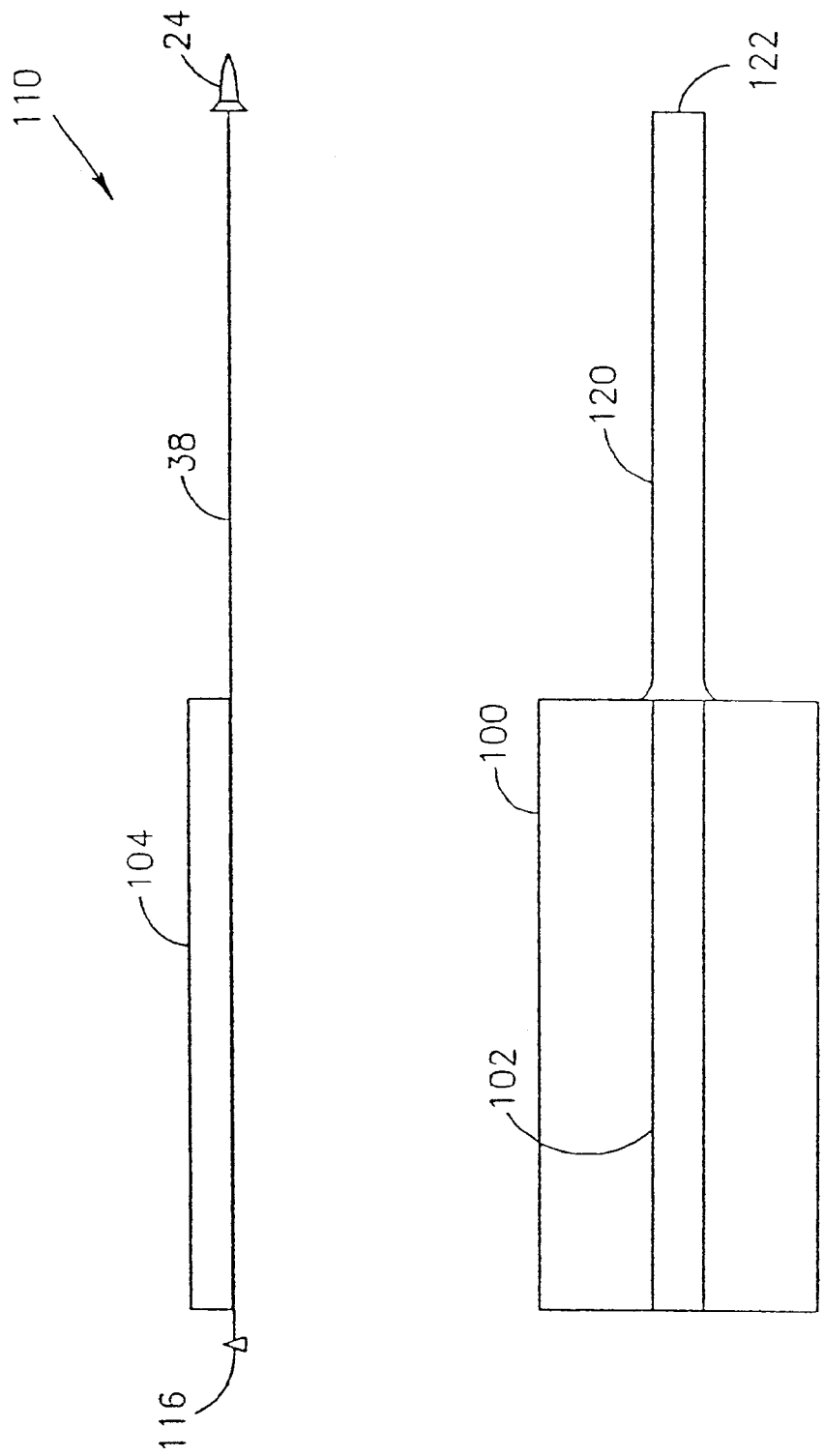
FIG. 4 is a schematic bottom view of a medical screwdriver and a compatible suture cartridge, in accordance with an embodiment of the present invention.

FIG. 4 is a schematic bottom view of a medical screwdriver 100 and a compatible suture cartridge 110, in accordance with an embodiment of the present invention. Screwdriver 100 comprises, along its bottom side, a slot 102, suitable for receiving a suture 38. Optionally, slot 102 is designed to tightly receive a suture holder 104 which prevents suture 38 from falling out through the long side of slot 102. In some embodiments of the invention, a suture holder 104 and suture 38 are packaged together in suture cartridge 110, optionally with screw 24. In some embodiments of the invention, suture holder 104 prevents suture 38 from moving longitudinally within slot 102. The distance along suture 38 between screw 24 and the beginning of suture holder 104 is optionally slightly larger than a shaft 120 of screwdriver 100, so as to allow for a certain amount of pull of suture 38 toward screw 24 due to rotation of shaft 120. Alternatively, suture holder 104 allows free longitudinal movement of suture 38 within slot 102. Optionally, suture 38 is connected, on an opposite end from screw 24 to an anchor 116 which prevents suture 38 from passing entirely through slot 102. The location of anchor 116 along suture 38 is optionally chosen in a manner which prevents suture 38 from dangling too freely near the patient. Alternatively or additionally, the location of anchor 116 is chosen so as to allow sufficient leeway of suture 38 due to the revolving of shaft 120.

Before each screw insertion procedure, suture holder 104 of a cartridge 110 is pushed into slot 102. Before or after insertion of suture holder 104 into slot 102, screw 24 is placed at a tip of a shaft 120 of screwdriver 100. After the screw is inserted to the bone, suture holder 104 is removed from slot 102, thus freeing suture 38 from screwdriver 100.

In some embodiments of the invention, after putting screw 24 and suture holder 104 in place, a sheath, such as sheath 90 (FIG. 3) is put in place surrounding shaft 120. Thus, suture 38 is captured within sheath 90 and cannot dangle freely.

Alternatively, cartridge 110 includes a sheath (not shown) which is connected (optionally as an integral part) to suture holder 104. Suture 38 is possibly located within the sheath in cartridge 110. In some embodiments of the invention, the sheath is brought to surround shaft 120 from its distal tip 122 and then suture 104 is pressed into slot 102. Alternatively or additionally, the sheath has a slot which allows shaft 120 to pass through when suture 104 is inserted to slot 102. Optionally, the sheath comprises an elastic material in which a slot opens only when force is applied. When the sheath is pressed against shaft 120 the slot opens and lets the sheath surround the slot, but immediately closes again to surround shaft 120 from all directions.

In some embodiments of the invention, shaft 120 comprises a slot in which suture 38 lays while the shaft revolves. Optionally, an additional suture holder is used to keep suture 38 in the slot of shaft 120. Possibly, a predetermined length of suture 38 is left free between the slot of shaft 120 and slot 102, to prevent tearing of the suture when shaft 120 turns.

It will be appreciated that the above described methods may be varied in many ways, including, performing a plurality of steps concurrently, changing the order of steps and changing the exact implementation used. It should also be appreciated that the above described description of methods and apparatus are to be interpreted as including apparatus for carrying out the methods and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. When used in the following claims, the terms "comprise," "include," "have" and their conjugates mean "including but not limited to."

What is claimed is:

1. A medical screwdriver for inserting a medical screw connected to a suture into a bone, comprising:
   a substantially straight shaft which holds a medical screw at its distal end;
   a motor adapted to rotate the shaft;
   a suture-receiving channel leading from the distal end of the shaft to a point distanced from the distal end of the shaft by at least 50% of the length of the shaft, and wherein the suture receiving channel comprises a through bore defined in the shaft.

2. In combination, a medical screw connected to a suture and a medical screwdriver for inserting the medical screw into a bone, comprising:
   a substantially straight shaft which holds the medical screw at its distal end;
   a motor adapted to rotate the shaft; and
   a suture-receiving channel leading from the distal end of the shaft to a point distanced from the distal end of the shaft by at least 50% of the length of the shaft.

3. A combination according to claim 2, wherein the suture receiving channel leads to a point distanced from the distal end of the shaft by the length of the shaft.

4. A combination according to claim 2, comprising a substantially straight stationary sheath which surrounds the shaft.

5. A combination according to claim 4 wherein the stationary sheath is removable.

6. A medical screwdriver for inserting a medical screw connected to a suture into a bone, comprising:
   a shaft adapted to hold a medical screw at its distal end;
   a motor adapted to rotate the shaft; and
   a suture-receiving channel leading from the distal end of the shaft to a point distanced from the distal end of the shaft by at least 50% of the length of the shaft,
   wherein the suture-receiving channel comprises a through bore in the shaft to define a hollow shaft, and
   wherein the hollow shaft is coupled to the motor through a gear pair.

7. A medical screwdriver for inserting a medical screw connected to a suture into a bone, comprising:
   a shaft adapted to hold a medical screw at its distal end;
   a motor adapted to rotate the shaft; and
   a suture-receiving channel leading from the distal end of the shaft to a point distanced from the distal end of the shaft by at least 50% of the length of the shaft,
   wherein the suture-receiving channel comprises a through bore in the shaft to define a hollow shaft, and
   wherein the hollow shaft is coupled to the motor through a shaft housing which defines a bore therethrough.

8. A medical screwdriver for inserting a medical screw connected to a suture into a bone, comprising:
   a shaft adapted to hold a medical screw at its distal end;
   a motor adapted to rotate the shaft; and
   a suture-receiving channel leading from the distal end of the shaft to a point distanced from the distal end of the shaft by at least 50% of the length of the shaft, and
   wherein the motor is held in a casing which defines a through channel, which channel leads from a first side of the casing close to a coupling to the shaft to an opposite side of the casing.

9. A medical screwdriver for inserting a medical screw connected to a suture into a bone, comprising:
   a shaft adapted to hold a medical screw at its distal end;
   a motor adapted to rotate the shaft;
   a suture-receiving channel leading from the distal end of the shaft to a point distanced from the distal end of the shaft by at least 50% of the length of the shaft, and
   a switch having a first position in which a suture located in the channel is held tightly and a second position in which the suture is free to move.

10. A medical screwdriver for inserting a medical screw connected to a suture into a bone, comprising:
    a shaft adapted to hold a medical screw at its distal end;
    a motor adapted to rotate the shaft;
    a suture-receiving channel leading from the distal end of the shaft to a point distanced from the distal end of the shaft by at least 50% of the length of the shaft,
    a stationary sheath which surrounds the shaft, and
    wherein the stationary sheath comprises a key which is adapted to fit in a respective notch in a casing of the motor.

11. A medical screwdriver for inserting a medical screw connected to a suture into a bone, comprising:
    a substantially straight shaft adapted to hold a medical screw at its distal end;
    a motor adapted to rotate the shaft;
    a suture-receiving channel leading from the distal end of the shaft to a point distanced from the distal end of the shaft by at least 50% of the length of the shaft,
    a substantially straight, stationary sheath which surrounds the shaft, and
    wherein the channel is defined between the stationary sheath and the shaft.

12. A medical screwdriver for inserting a medical screw connected to a suture into a bone, comprising:
    a substantially straight shaft adapted to hold a medical screw at its distal end;
    a motor adapted to rotate the shaft;
    a suture-receiving channel leading from the distal end of the shaft to a point distanced from the distal end of the shaft by at least 50% of the length of the shaft,
    a substantially straight, stationary sheath which surrounds the shaft, and
    wherein the stationary sheath comprises a distal collapsible shield which is adapted to cover, in the absence of an axially applied force, at least a portion of a screw held by the shaft.

13. A medical screwdriver for inserting a medical screw connected to a suture into a bone, comprising:
    a substantially straight shaft adapted to hold a medical screw at its distal end;
    a substantially straight stationary sheath which surrounds the shaft;
    a motor adapted to rotate the shaft so as to push the screw into a bone, and
    wherein the stationary sheath comprises a distal collapsible shield which is adapted, in the absence of force, to cover at least a portion of a screw held by the shaft.

* * * * *